United States Patent
LaBelle et al.

(10) Patent No.: US 10,323,008 B2
(45) Date of Patent: Jun. 18, 2019

(54) UNIQUE SELF-ASSEMBLED POLY-AMIDOAMINE POLYMERS AND THEIR ELECTROCHEMICAL REACTIVITY

(71) Applicant: ARIZONA BOARD OF REGENTS ON BEHALF OF ARIZONA STATE UNIVERSITY, Scottsdale, AZ (US)

(72) Inventors: Jeffrey LaBelle, Tempe, AZ (US); Trevor Saxman, Glendale, AZ (US); Brittney Haselwood, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 9 days.

(21) Appl. No.: 15/316,468

(22) PCT Filed: Jun. 5, 2015

(86) PCT No.: PCT/US2015/034495
§ 371 (c)(1),
(2) Date: Dec. 5, 2016

(87) PCT Pub. No.: WO2015/188107
PCT Pub. Date: Dec. 10, 2015

(65) Prior Publication Data
US 2017/0190674 A1 Jul. 6, 2017

Related U.S. Application Data

(60) Provisional application No. 62/008,923, filed on Jun. 6, 2014.

(51) Int. Cl.
*C08G 73/02* (2006.01)
*C08G 83/00* (2006.01)
(Continued)

(52) U.S. Cl.
CPC ......... *C07D 245/04* (2013.01); *C08G 73/028* (2013.01); *C08G 83/003* (2013.01); *G01N 33/66* (2013.01)

(58) Field of Classification Search
None
See application file for complete search history.

(56) References Cited

U.S. PATENT DOCUMENTS

| | | |
|---|---|---|
| 6,287,765 B1 | 9/2001 | Cubicciotti |
| 7,694,582 B2 | 4/2010 | Hayakawa et al. |
| | (Continued) | |

FOREIGN PATENT DOCUMENTS

| | | |
|---|---|---|
| WO | 2001006245 | 1/2001 |
| WO | 2012052758 | 4/2012 |
| | (Continued) | |

OTHER PUBLICATIONS

Dai et al., "Mesoporous carbon amperometric glucose sensors using inexpensive, commercial methacrylate-based binders," Analytica Chimica Acta, Aug. 2012, pp. 27-34, vol. 738.
(Continued)

*Primary Examiner* — Rachel Kahn
(74) *Attorney, Agent, or Firm* — Gavin J. Milczarek-Desai; Quarles & Brady LLP

(57) ABSTRACT

Synthesis of novel and unique PAMAM (poly-amidoamine) polymers. PAMAM polymers can be grown by systematic alternation between ethylenediamine (EDA) and methacrylate. By taking advantage of the alternating terminal ends, successive generations G1 and G0.5 were combined under acidic conditions with Pluronic P123 as a liquid-crystal template. The resulting polymer was imaged with TEM and the product was circular and amorphous of no characteristic size ranging between about 5 nm to about 600 nm, with remarkable electrochemical activity unseen in any of the
(Continued)

generations of PAMAM. Applications of this electroactive poly-amidoamine organic polymer include use as a new electron transfer reagent for amperometric biosensors.

1 Claim, 14 Drawing Sheets

(51) Int. Cl.
*G01N 33/66* (2006.01)
*C07D 245/04* (2006.01)

(56) References Cited

U.S. PATENT DOCUMENTS

| | | | |
|---|---|---|---|
| 7,854,173 | B2 | 12/2010 | Cheng et al. |
| 2007/0155712 | A1 | 7/2007 | Zahn et al. |
| 2009/0131657 | A1 | 5/2009 | Staffel et al. |
| 2009/0137887 | A1 | 5/2009 | Shariati et al. |
| 2009/0203980 | A1 | 8/2009 | Carlson et al. |
| 2010/0012521 | A1 | 1/2010 | Feldman et al. |
| 2015/0268108 | A1 | 9/2015 | LaBelle et al. |

FOREIGN PATENT DOCUMENTS

| | | |
|---|---|---|
| WO | 2013025616 | 2/2013 |
| WO | 2014052470 | 4/2014 |
| WO | 2015188107 | 12/2015 |

OTHER PUBLICATIONS

Sun et al., "Electrochemical sensor for simultaneous detection of ascorbic acid, uric acid and xanthine based on the surface enhancement effect of mesoporous silica," Sensors and Actuators B, Sep. 2009, pp. 641-645, vol. 141, issue 2.

Peterson et al., "Synthesis and CZE analysis of PAMAM dendrimers with an ethylenediamine core," Proc. Estonian Acad. Sci. Chem., 2001, pp. 156-166, vol. 50, issue 3.

Landskron and Ozin, "Periodic mesoporous dendrisilicas," Science, Nov. 2004, pp. 1529-1532, vol. 306, issue 5701.

Patent Cooperation Treaty, International Searching Authority, "International Preliminary Report on Patentability for PCT/US15/34495," 4 pages, dated Dec. 6, 2016.

Patent Cooperation Treaty, International Searching Authority, "Written Opinion of the International Searching Authority for PCT/US15/34495," 3 pages, dated Sep. 15, 2015.

Patent Cooperation Treaty, International Searching Authority, "International Search Report for PCT/US15/34495," 2 pages, dated Sep. 15, 2015.

Patent Cooperation Treaty, International Searching Authority, "International Preliminary Report on Patentability for PCT/US13/61711," 6 pages, dated Mar. 31, 2015.

Patent Cooperation Treaty, International Searching Authority, "Written Opinion of the International Searching Authority for PCT/US13/61711," 5 pages, dated Feb. 7, 2014.

Patent Cooperation Treaty, International Searching Authority, "International Search Report for PCT/US13/61711," 3 pages, dated Feb. 7, 2014.

UNIQUE SELF-ASSEMBLED POLY-AMIDOAMINE POLYMERS AND THEIR ELECTROCHEMICAL REACTIVITY

CROSS-REFERENCE TO RELATED APPLICATIONS

This application is a 371 application of PCT/US2015/034495 filed Jun. 5, 2015, which claims priority to U.S. Provisional Patent Application No. 62/008,923 filed on Jun. 6, 2014.

BACKGROUND OF THE INVENTION

Biomarker electrochemical testing constantly demands greater degrees of sensitivity and specificity. Specifically, medical conditions that require point of care testing like diabetes are increasing in prevalence in the United States. With increasing demand, the market requires high quality tests that cost less to produce. One approach to this problem is utilizing highly ordered nanomaterials. The use of mesoporous carbon electrodes has shown to produce a remarkable increase in the sensitivity and the specificity of electrochemical testing.

Nanoparticles and nano-scale structures have become a cornerstone of point of care testing. Nanoparticles can be conjugated to enzymes to alter the frequency at which they are best detected, while mesoporous materials have been used as electrodes for detecting small molecules like glucose, uric acid, lactate, and other similar molecules. Carbon electrodes are cheap and effective ways of producing electrochemical sensors for biochemical detection. Alteration of the structure of the carbon in these electrodes allows for more accurate detection.

Creating tailored mesoporous materials is a step forward to achieving a higher degree of sensitivity and level of detection. It has been demonstrated that the type of material used to detect has a significant effect on the performance of the sensor. These results show that mesoporous silica outperformed a mesoporous carbon electrode for the detection of ascorbic acid, uric acid, and xanthine. Although mesoporous carbon out performs silica for the detection of lactate and glucose, it is not sufficient to merely control the physical features of the mesoporous materials, they must be tailored specifically to the analyte trying to be detected. Therefore, there is a need for creating tailored materials that may provide a higher degree of sensitivity and level of detection than is conventionally available.

SUMMARY OF THE INVENTION

This invention relates to a polymer capable of conducting electrons through solution, in the presence of a metal working electrode, by mobilizing metal ions into the solution.

Some embodiments provide a chemical composition that includes:

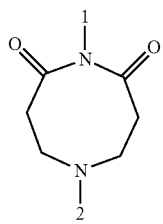

In which 1 includes $(CH_2CH_2)[N(CH_2CH_2CONHCH_2CH_2N^*)_2]_2$; and 2 includes $(CH_2CH_2)[N(CH_2CH_2CONHCH_2CH_2N(CH_2CH_2CO^*)_2)_2]_2$.

The "*" indicates the point of attachment. Other embodiments provide a chemical composition that includes a polymer capable of conducting an electric current through a solution, the polymer including at least one of molecule 1 (as described above) and one of molecule 2 (as described above) and configured to perform in-vivo electrochemical biomarker detection.

Further embodiments provide a method of performing biomarker detection including synthesizing a polymer capable of conducting an electric current through a solution, the polymer including at least one polyamide polymer and configured to perform in-vivo electrochemical biomarker detection. The method further includes performing in-vivo electrochemical biomarker detection using the polymer.

These and other aspects will be apparent upon reference to the following detailed description and figures. To that end, any patent and other documents cited herein are hereby incorporated by reference in their entirety.

DETAILED DESCRIPTION OF THE INVENTION

Figure 1:
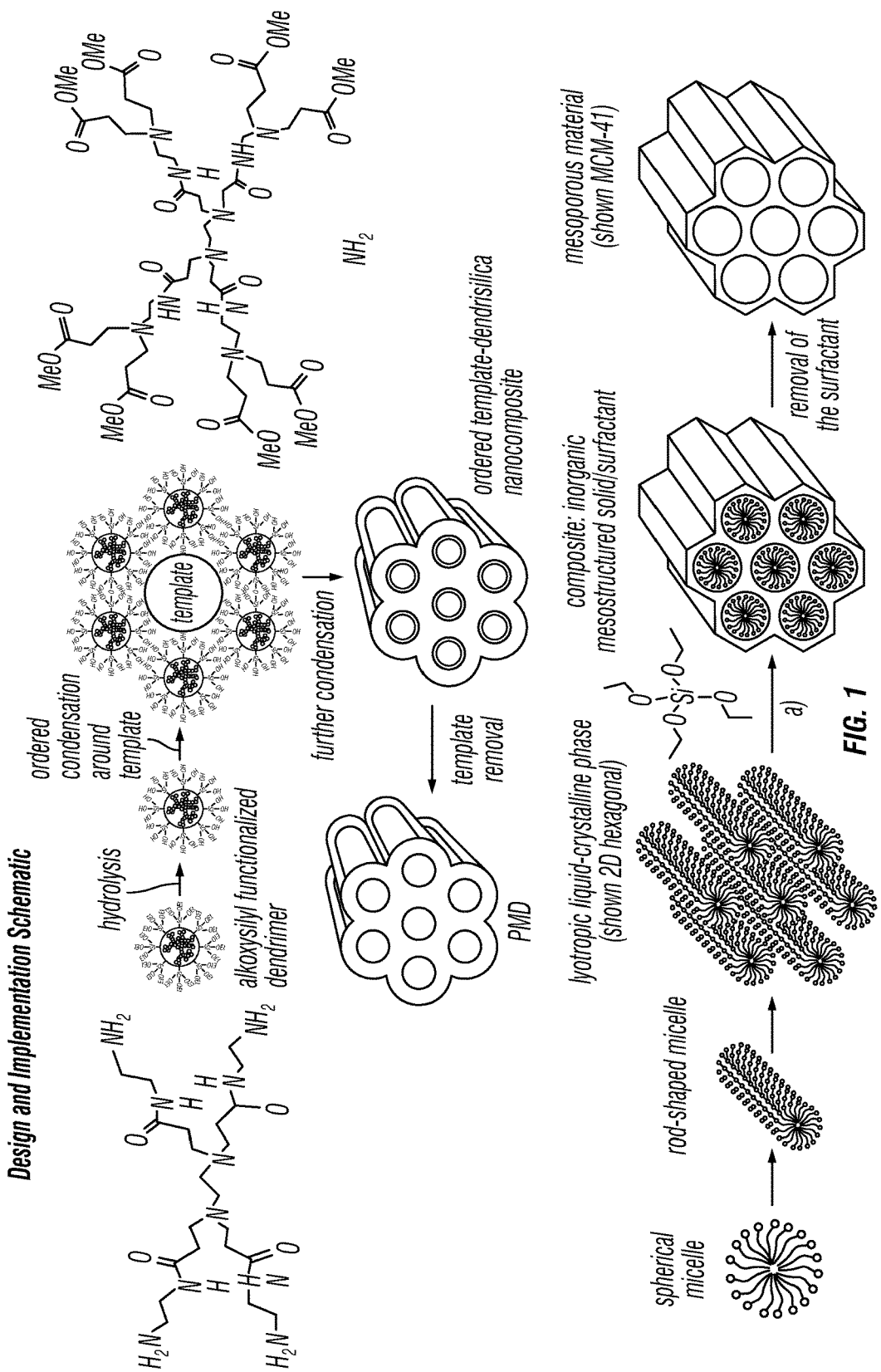
FIG. 1 depicts a schematic of self-assembly of a mesoporous material from a polymer composition.

This disclosure relates to regents for electrochemical detection, energy storage, and alternative energy sources. More specifically, this invention relates to polymers capable of conducting electrons through solution, in the presence of a metal working electrode, by mobilizing metal ions into the solution. This invention has been used to create a metal polymer electrolytic cell, capable of operating at high currents at low voltages for the purposes of electrochemical detections, energy storage, and other alternative energy technologies.

In an embodiment, the synthesis of a novel and unique PAMAM (poly-amidoamine) polymer is disclosed. PAMAM polymers can be grown by systematic alternation between ethylenediamine (EDA) and methacrylate. By taking advantage of the alternating terminal ends, successive generations G1 and G0.5 were combined under acidic conditions with Pluronic P123 as a liquid-crystal template. The resulting polymer was imaged with TEM and the product was circular and amorphous of no characteristic size ranging between about 5 nm to about 600 nm. Though generally disordered, this polymer demonstrates remarkable electrochemical activity substantially unseen in any of the generations of PAMAM. This electroactive poly-amidoamine organic polymer can be used as a new electron transfer reagent for amperometric biosensors.

Nano-scale materials provide three critical features that effect how a sensor performs: filtration, encapsulation, and surface area. The small pore size in these materials prevents large interfering structures from reaching the surface of the electrode. Other fields of research like mass spectrometry also exploit this filtration effect; nanoporous or mesoporous materials allow small molecules to pass through where they interact with antibodies before being ionized. This filtration effectively removes a significant source of noise and error in whole blood or serum samples. Concordantly the small diameters can also be used to encapsulate enzymes and antibodies. Encapsulation increases the number of enzymes that are at the electrode surface, while decreasing artifact from Brownian motion in solution. The features of encapsulation have been utilized to create a sensor for lactate. These features alone demonstrate a significant need for being able to control the structural features of materials on a nano-scale.

Polyamidoamine polymers (PAMAM) have been extensively studied for their dendrimeric properties. They can be created at room temperature, under standard conditions, to produce high product yields. Starburst and other generations of PAMAM have been studied as drug delivery vehicles, and a variety of other applications including electrochemical testing. PAMAM dendrimers can be synthesized in a variety of ways, with interchangeable linking units modifying the properties based on the desired application and design. PAMAM can be used like a molecular level Napoleonic interchangeable parts system, where each successive generation provides a specific tailored attribute to the behavior of the dendrimer. It is this high degree substitutability that makes PAMAM dendrimers an ideal polymer to study the synthesis of mesoporous structures.

PAMAM's stepwise synthesis provides an ideal experimental material to provide a proof of concept for utilizing the liquid-crystal template method for creating specifically tailored nano-structured materials. The two reactions in PAMAM synthesis happen under mild conditions that are compatible with a templating solution. As shown in FIG. 1, successive generations of PAMAM dendrimers have terminal functional groups that readily react with each other linking the two generations together around the template. Concentric symmetry allows for growth in all directions simultaneously that can be controlled by the number of terminal groups present on the generation of PAMAM.

EXAMPLE 1

Materials:

All chemicals were purchased from Sigma-Aldrich. Ethylenediamine 99%, Methyl Acrylate 99%, Methanol Anhydrous 99%, Pluronic P123, n-butanol. Silica Gel, NaCl 99%, HCl solution (1M).

Methods:

Synthesis of G−0.5

2 grams (1.8 ml) of EDA was dissolved into 100 ml of methanol and cooled in an ice bath. 13.6 mmol (1.112 ml) of methyl acrylate was added dropwise under stirring. The solution was allowed to react for 168 hours at room temperature. The excess methyl acrylate was removed under vacuum. The remaining viscous liquid was purified via silica gel column chromatography with a 10:1 dichloromethane/methanol eluant.

Synthesis of G0

17.85 grams (16.065 ml) of EDA was dissolved into 10 ml of methanol and cooled to −30° C. in dry ice. 1.37 g of G−0.5 PAMAM was dissolved into 2.5 ml of methanol and cooled to −30° C. in dry ice. The dendrimer solution was added gradually to the EDA solution without significant change in temperature. The solution was allowed to warm to room temperature and react for 168 hours at room temperature (25° C.). 100 ml of n-butanol was added to the solution, and the excess EDA was distilled off with the n-butanol.

Synthesis of G0.5

1.37 grams of G0 PAMAM was dissolved into 20 ml of methanol and cooled in an ice bath. 23.2 mmol (1.897 ml) of methyl acrylate was added dropwise under stirring. The solution was allowed to react for 96 hours at room temperature and 24 hours at 45° C. The excess methyl acrylate was removed under vacuum. The remaining viscous liquid was purified via silica gel column chromatography with a 10:1 dichloromethane/methanol eluant.

Synthesis of MC-A 1.85 grams of NaCl and 0.336 g of Pluronic 123 were dissolved into 2.8 ml of 1M HCL. To this solution 0.752 grams of G0.5 PAMAM and 0.188 grams of G0 PAMAM were added successively under vigorous stirring at room temperature. The mixture was stirred at room temperature for 24 hours. The solution was then incubated at 45° C. for 24 hours. All solid material was filtered out, and an additional (3 ml) of G0 was added under vigorous stirring to the solution. This solution was stored at 0° C. for 72 hours. The amber solution was dried via vacuum distillation, and orange crystals precipitated from the solution. The surfactant cores were removed with a 25:1 acetone/HCl mixture for 2 days at 40° C. The extraction product was filtered off and washed with acetone, leaving a waxy orange coagulation of crystals.

Synthesis of MC-B 1.85 grams of NaCl was dissolved into 2.8 ml of 1M HCL, any excess crystals were filtered out via vacuum filtration. 0.336 g of Pluronic 123 was then added to the solution and was allowed to mix until homogeneous. To this solution 0.6 grams of G0.5 PAMAM was added and allowed to mix completely, subsequently 0.3 grams of G0 PAMAM were added dropwise under vigorous stirring at room temperature (25° C.). The mixture was stirred at room temperature (25° C.) for 24 hours. The solution was then incubated at 45° C. for 24 hours. The liquid phase was filtered, the amber solution was dried via vacuum distillation, and orange crystals were precipitated from the solution. The surfactant core was removed with a 25:1 acetone/HCl mixture for 2 days at 40° C. The extraction product was filtered off and washed with acetone, leaving a waxy orange coagulation of crystals.

CV

Using the mass of 100 mM, 0.032 g/mL ferricyanide as a reference, solutions ranging from 0.01 g/mL to 0.08 g/mL of MC-A was prepared in PBS. The sample was tested on a screen-printed three lead carbon electrode. The sample was run from 1.5 to −1.5 for six segments to obtain a CV.

Results:

The resulting polymer from the synthesis is a orange-amber soft solid, stable at room temperature (25° C.). Two synthesis lots MC-A and MC-B differed only by minor changes in the final synthesis step. Completely dried MC-A physically was more like a dry crystal, though soft and easily compressed into other shapes. MC-B retained a waxy, almost gel like, soft consistency and was lighter in color. Both MC-A and MC-B are equally soluble in water, though MC-A seems to dissolve slightly faster then MC-B.

Figure 2A:
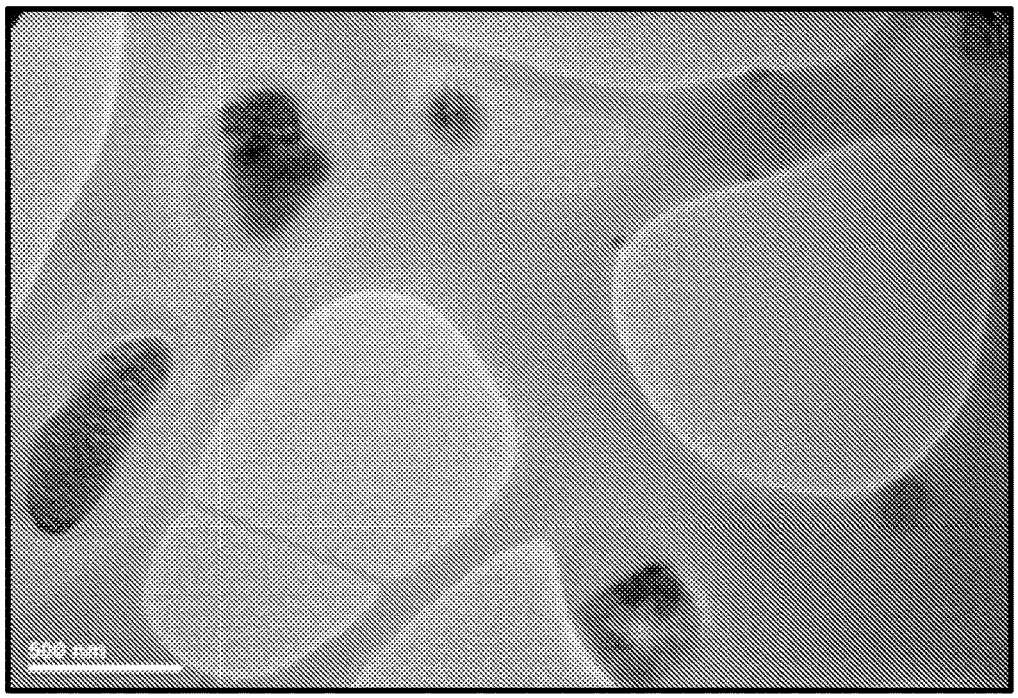
FIG. 2A depicts TEM (transmission electron microscopy) images of EPOP (Electroactive Poly(amidoamine) Organic Polymers) particles under standard conditions.
Figure 2B:
FIG. 2B depicts TEM images of EPOP particles under standard conditions.

As shown in FIGS. 2A and 2B, TEM imaging of MC-B shows amorphous or circular particles with no particular shape or size. The large samples appear to have small circular structures, which might represent pores, and a topographical surface. As a whole the material is unordered and lacks the mesopores seen in the synthesis of porous organosilicates and carbon compounds.

Figure 3:
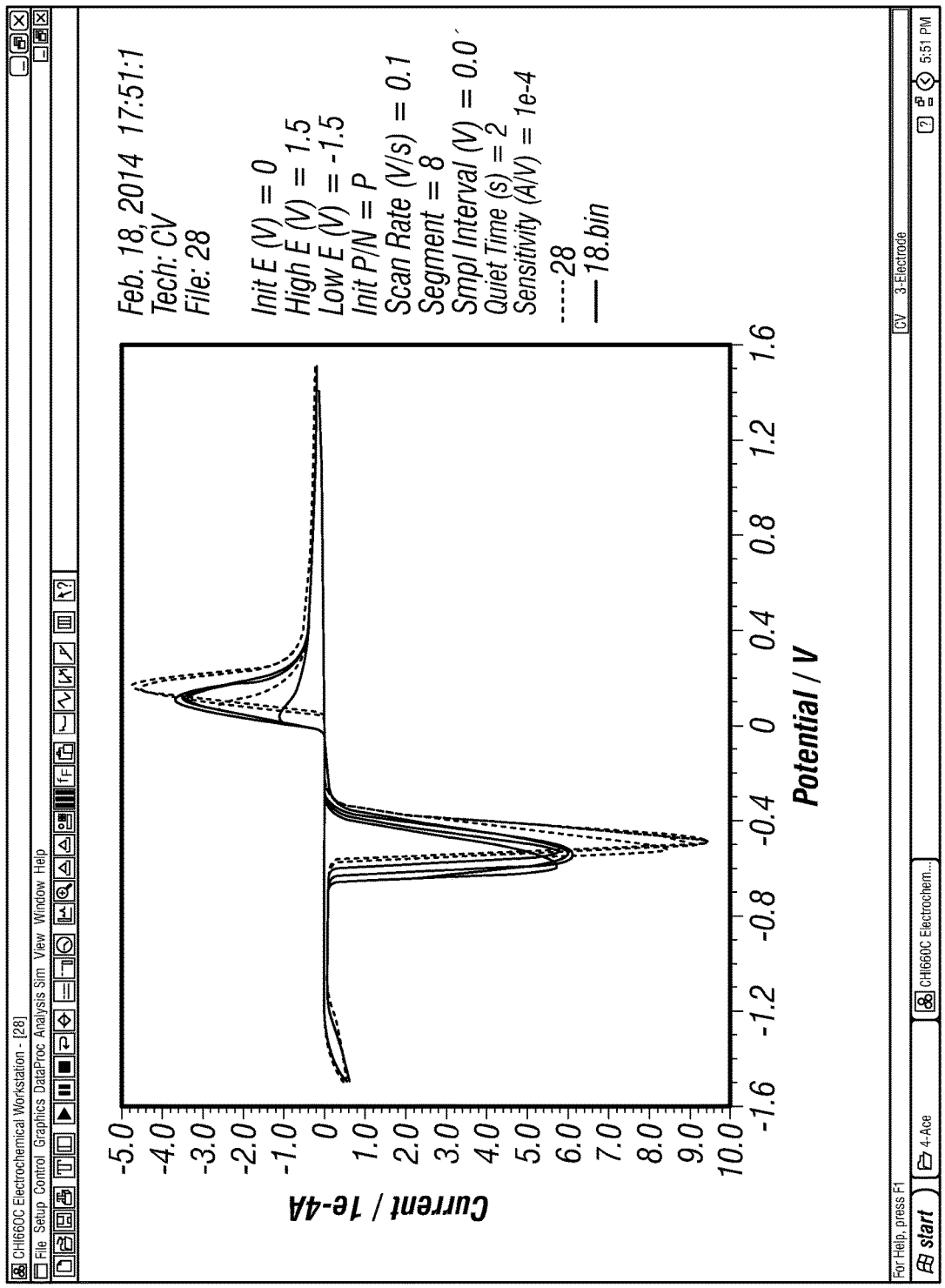
FIG. 3 depicts CV data that illustrate the electrical activity of EPOP, with inset electrical activity of Poly(amidoamine), or PAMAM. CV of EPOP is shown with average peaks around −0.55V and 0.25V. The peaks shift to a small degree based on the concentration of EPOP in the solution. When combined with other electro active species the CV of EPOP changes in unique patterns based on the other electro active substance.
Figure 4:
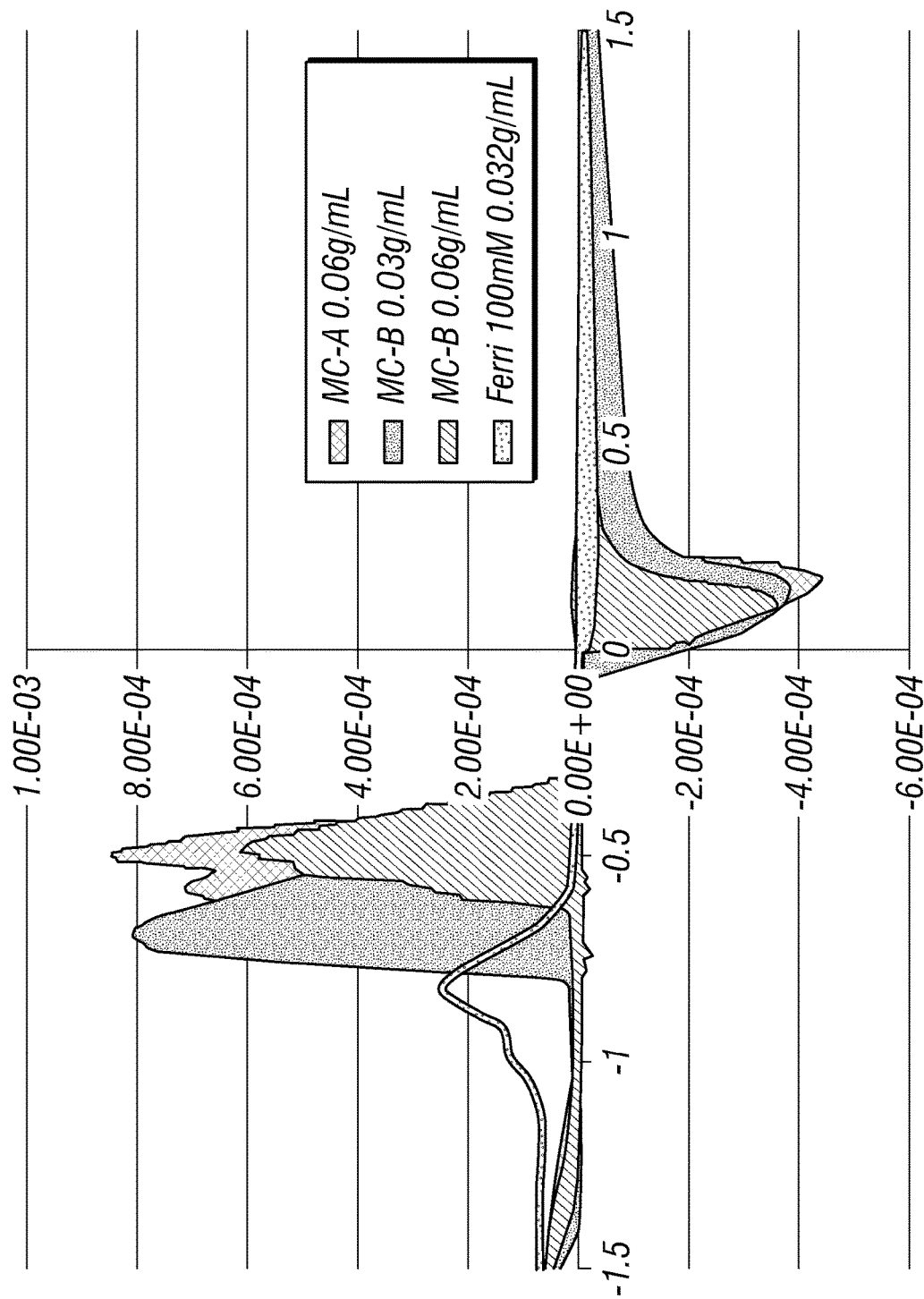
FIG. 4 depicts CV data that illustrate electrochemical activity of EPOP as compared to FERRI.
Figure 5:
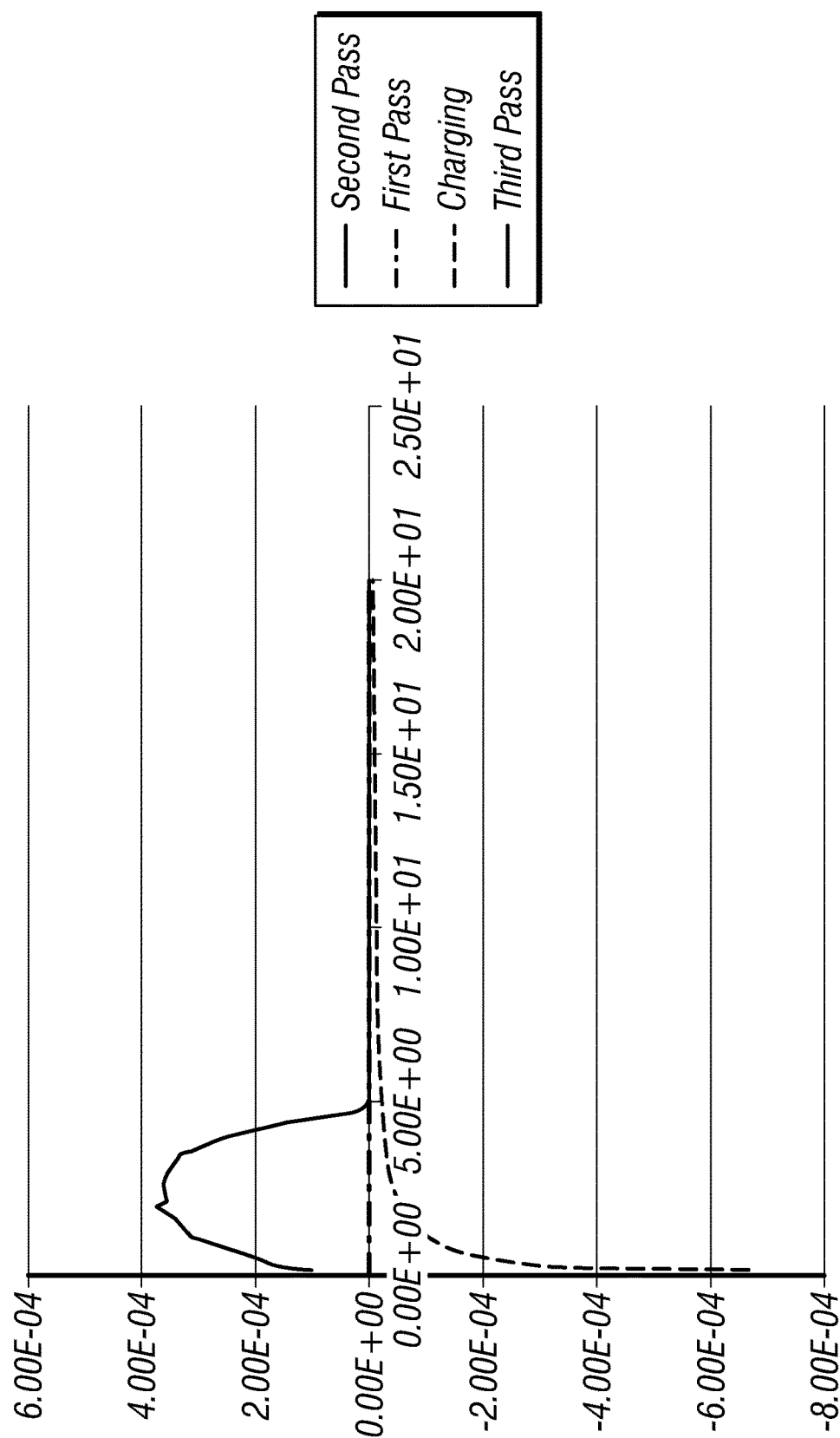
FIG. 5 depicts data that illustrate a battery AMP-it. EPOP is shown to perform differently than a classical capacitor. The minimum activating current in FIG. 5 is about −0.4V. The material is sensitive to pH, which has effects on the magnitude and the duration of discharge.
Figure 6:
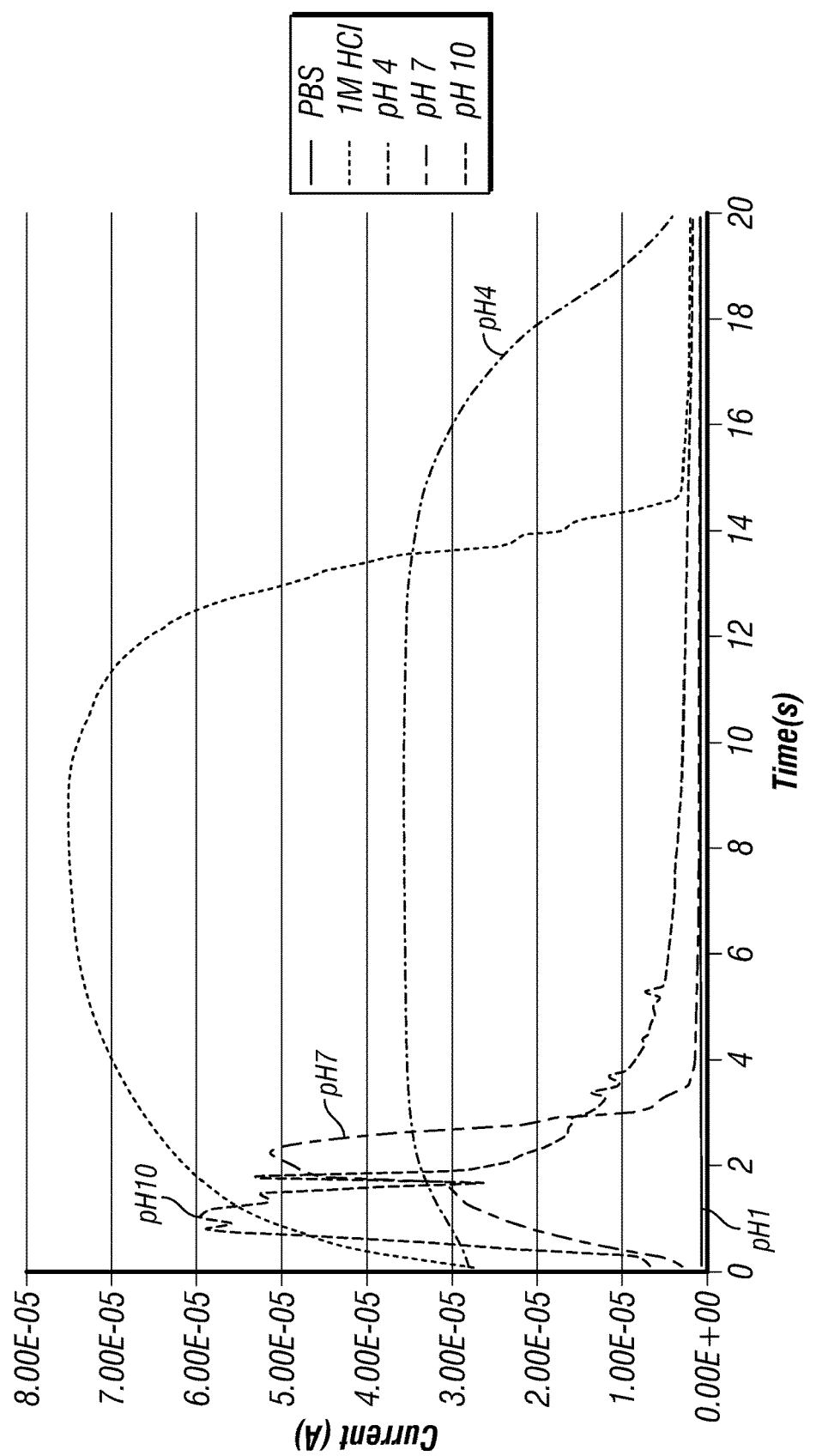
FIG. 6 depicts data that illustrate that very acidic solutions significantly reduce the function of EPOP, while mildly acidic solutions have a moderating effect.
Figure 7:
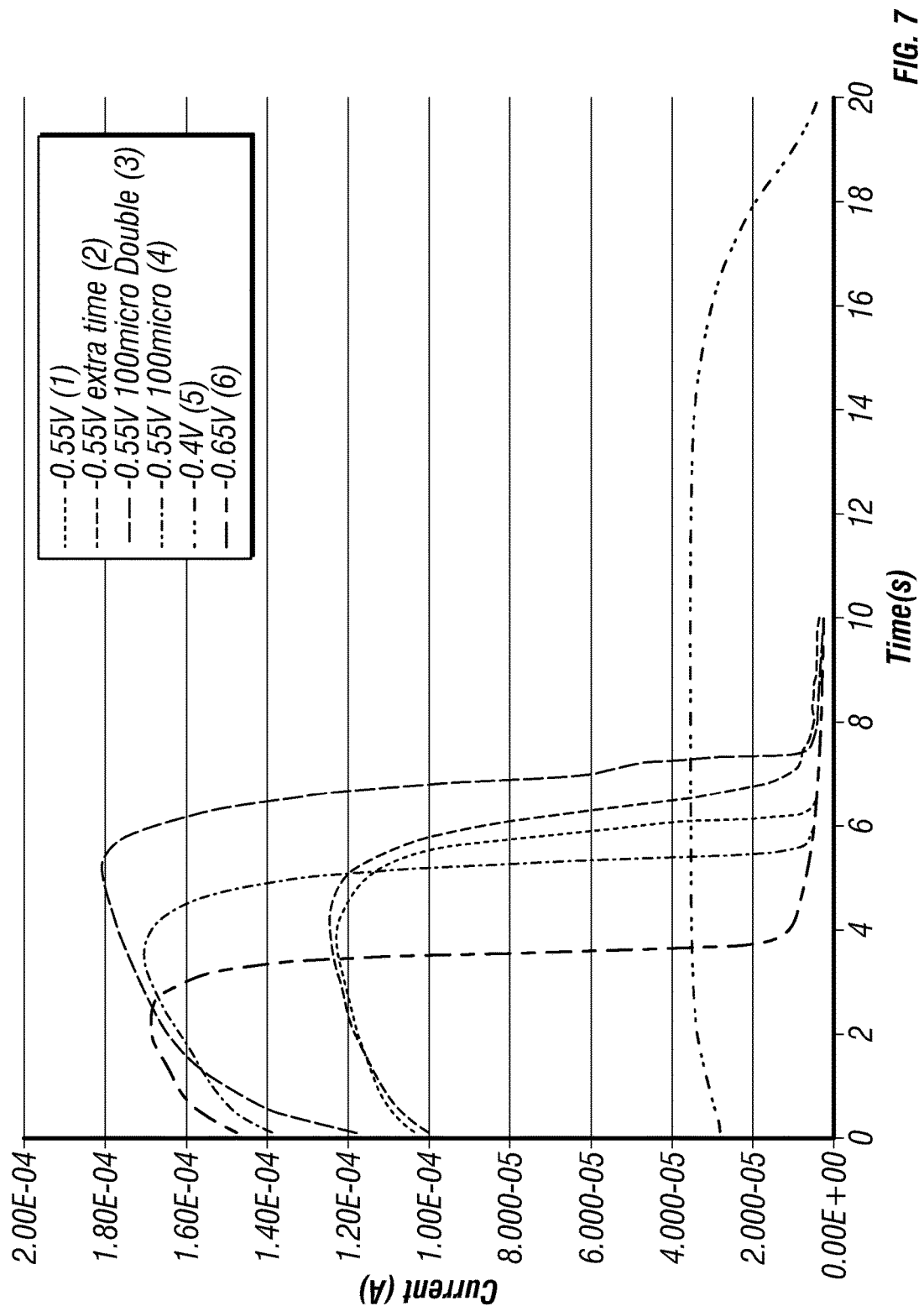
FIG. 7 illustrates data that demonstrate that pH is not the only fact that has an effect on the way EPOP behave, reversal voltage effects the peak current −0.55V −0.4V −0.65V, length of charge time 10 extra seconds, the amount of sample 50 μL increased to 100 μL, double charging the sample.
Figure 8:
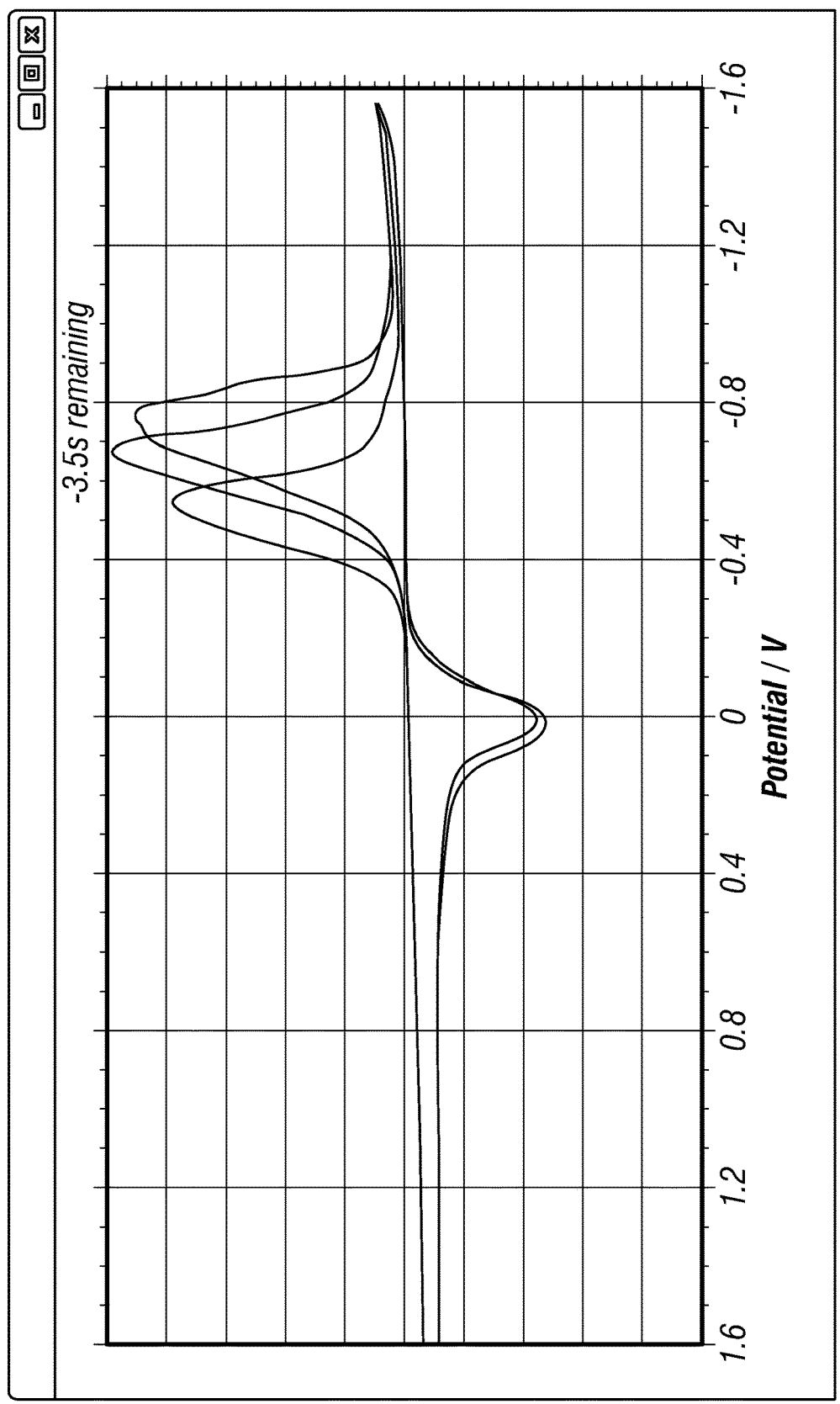
FIG. 8 depicts data illustrating electroactive properties of a polymer composition on an electrode system using carbon, carbon, and copper.
Figure 9:
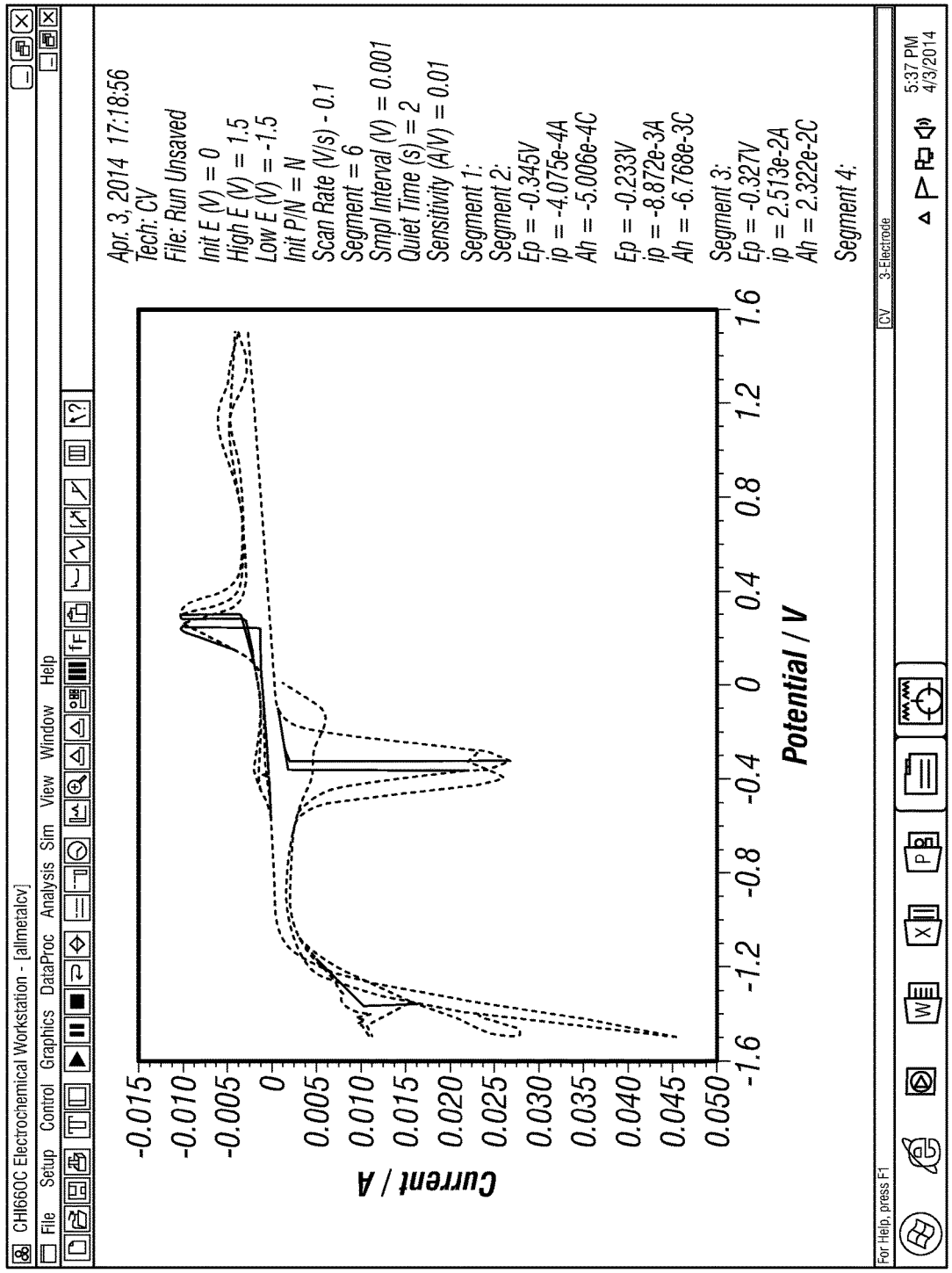
FIG. 9 depicts data illustrating electroactive properties of a polymer composition achieved on an electrode system using nickle, carbon, and copper.
Figure 10:
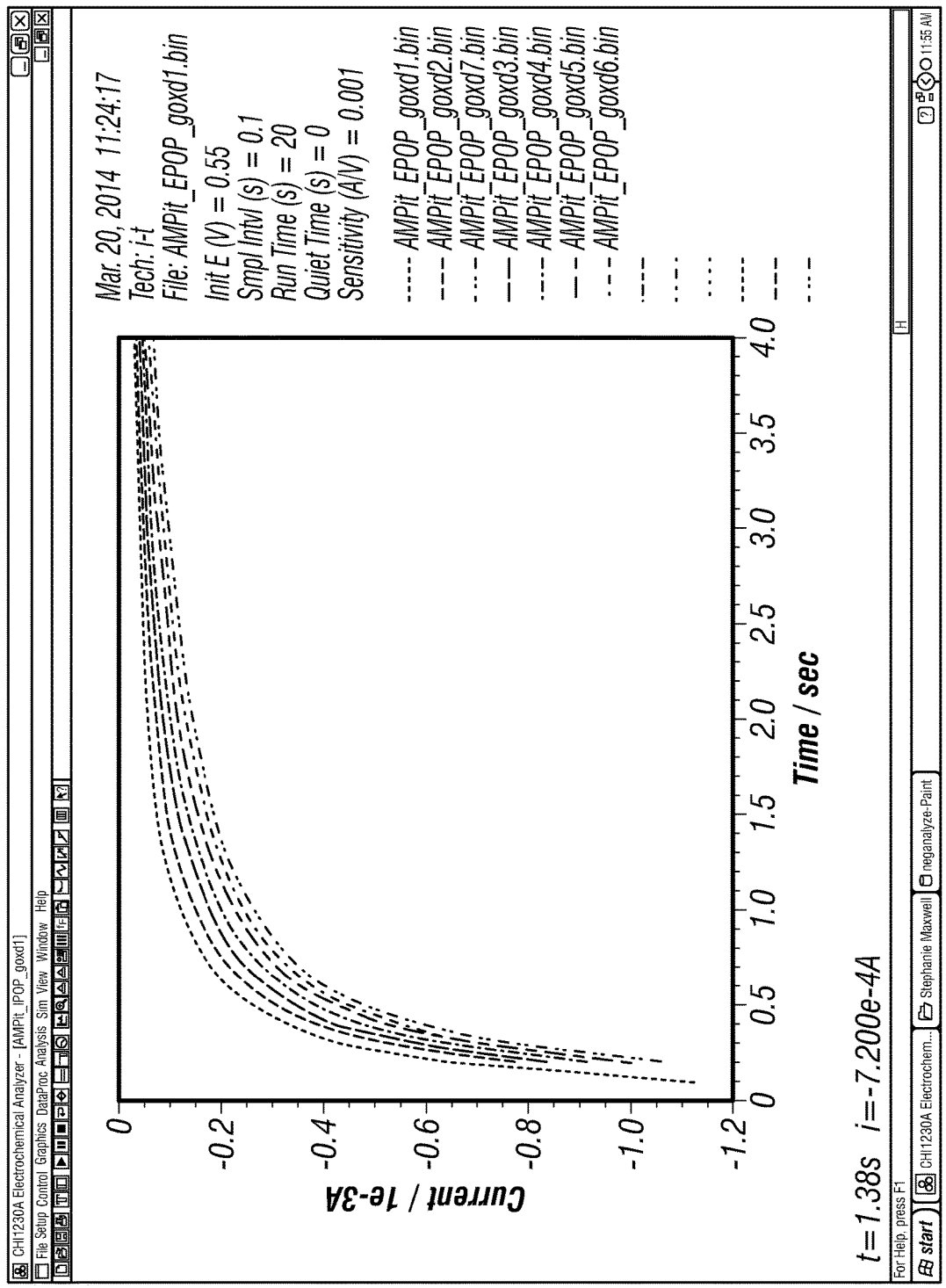
FIG. 10 depicts data illustrating electrochemical detection of glucose molecules using a polymer composition as a detection sensor.
Figure 11:
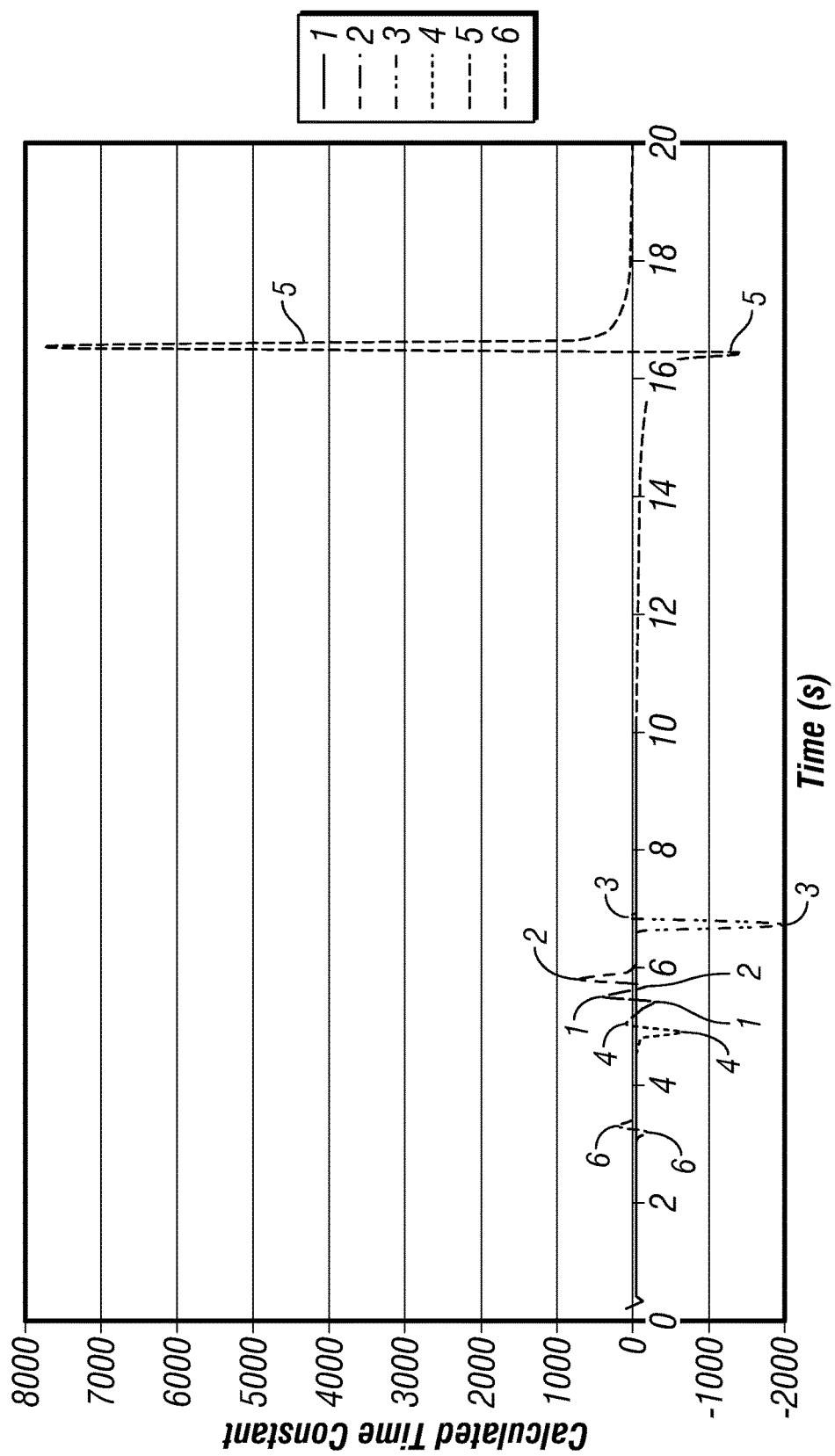
FIG. 11 illustrates the change in calculated time constants of the solutions of an electroactive compound under different conditions. Average time constants: 1, 1.42E+01; 2, 2.45E+01; 3, 4.93E+00; 4, 4.65E+00; 5, 2.07E+02; 6, 5.56E+00. Total Current: 1, 6.91E−03; 2, 7.50E−03; 3, 1.14E−02; 4, 8.46E−03; 5, 6.23E−03; 6, 5.99E−03. Capacity: 1, 1.55E−02; 2, 1.73E−02; 3, 2.99E−02; 4, 2.02E−02; 5, 2.72E−02; 6, 1.29E−02.
Figure 12:
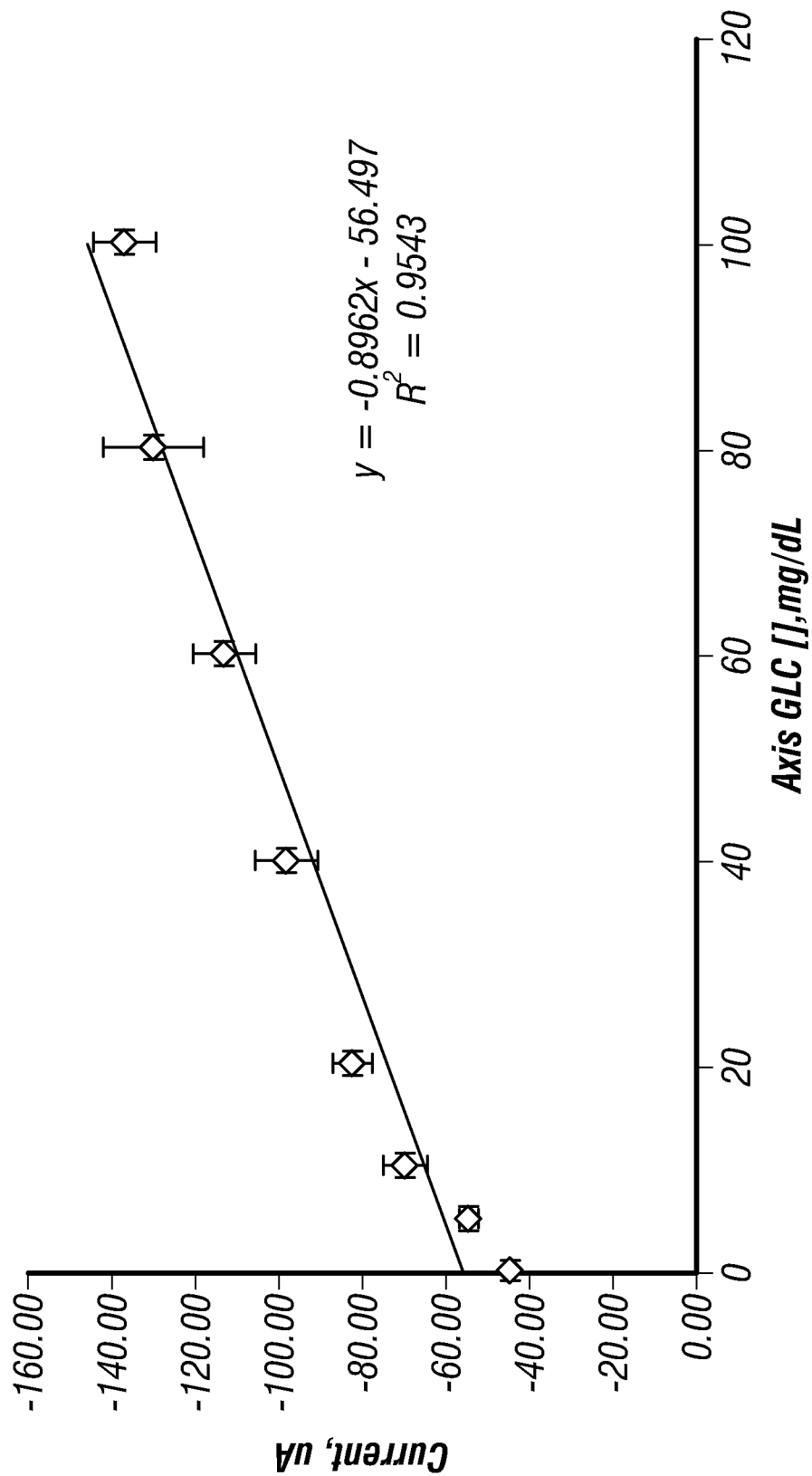
FIG. 12 illustrates a linear standard curve based on the data from glucose detection.
Figure 13A:
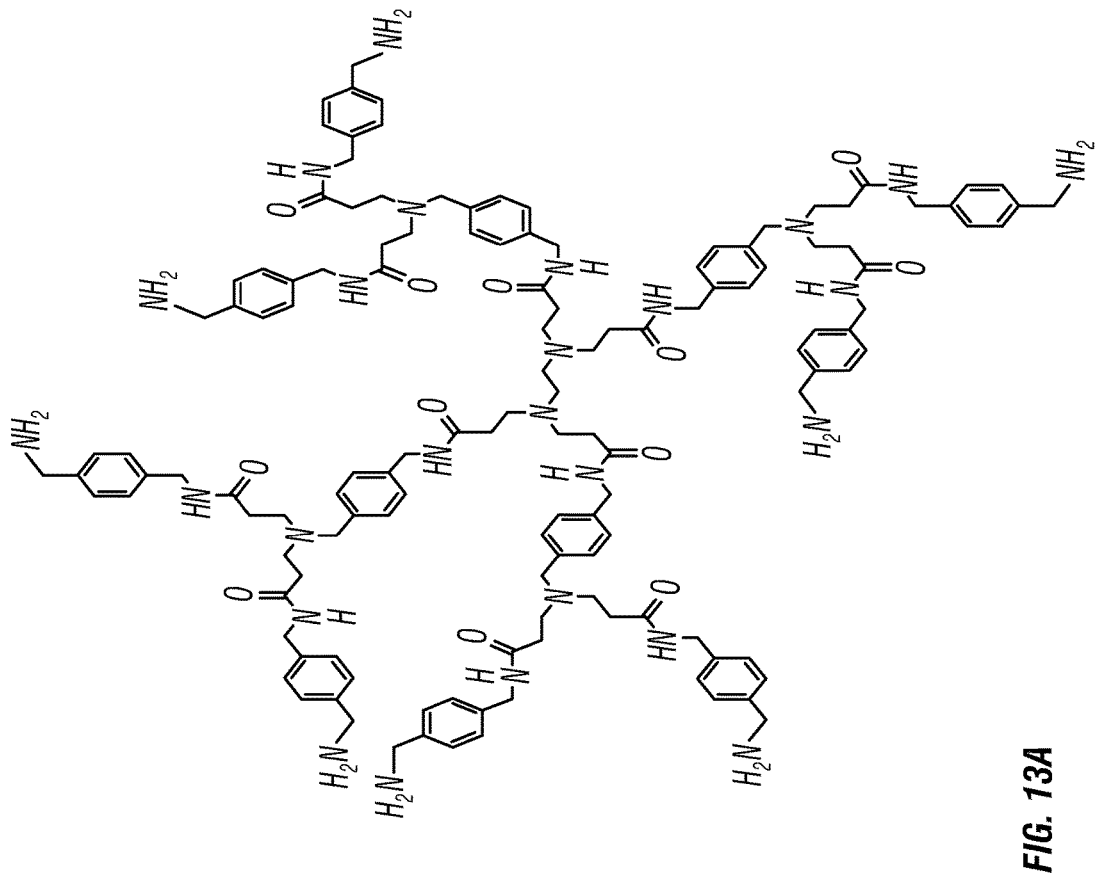
FIG. 13A illustrates a polymer compostion of the invention.
Figure 13A:
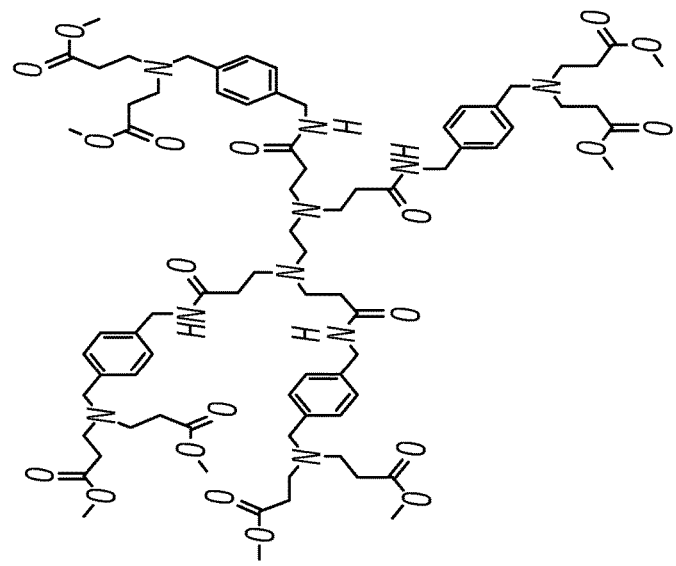
Figure 13B:
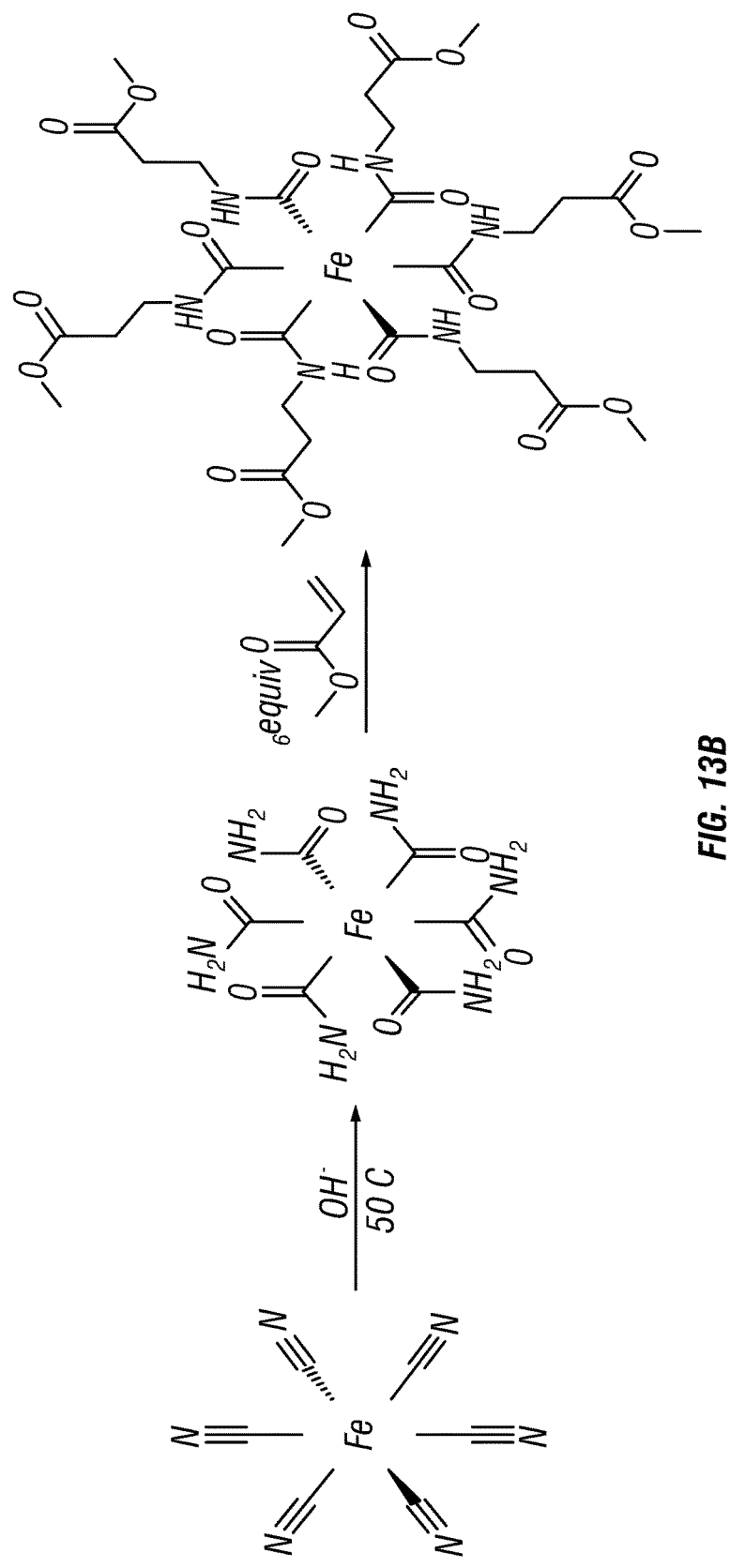
FIG. 13B illustrates a polymer compostion of the invention.

As shown in FIG. 3, both MC-A and MC-B have similar responses on cyclic voltammetry peaking around −0.5 and 0.2 volts. Without any other chemicals present EPOP shows oxidative and reductive potential at low voltage, nearing a milliamp at negative voltages. Unlike exhaustive oxidation and reduction reactions as sequential passes are made on the sample the current increases, stepwise, until the peak current is obtained. The sample remained capable of returning to peak current even after seventeen cycles. The precursor generations of PAMAM show substantially no significant electrical activity.

The physical differences of MC-A and MC-B, based on the TEM images and the electrochemical similarity of the two samples, could possibly be a difference in the average particle size of the material. The second addition of G0 to MC-A provides linkages between molecules that have already grown to a significant size. It is possible that by modifying the conditions of the final step that average particle size could be controlled. PAMAM generations are grown at cold temperatures (below 25° C.), and a room temperature step (25° C.) could easily produce less ordered particles.

It is also possible that an ordered structure was not formed because of an incompatibility of the PAMAM dendrimers and the liquid-crystal templating method used. EPOP is completely insoluble in polar organic solvents, and soluble in water. Acetone, which is a compatible solvent for Pluronic P123, caused EPOP to aggregate and clump. It is therefore reasonable to assume that a similar interaction may exist with P123, making it impossible to coordinate around the template. It is possible that a different templating method would make it possible to coordinate the structure of the material. Further attempts at synthesis, could attempt to control these variables.

Regardless of the structure of the material, it is remarkably electroactive and can function as a sensor as shown in FIGS. 4-12. No other PAMAM related synthesis uses the polymer as the substance that is electroactive.

The claims are not meant to be limited to the materials and methods, examples, and embodiments described herein.

The invention claimed is:

1. A chemical composition comprising:
   one or more polymers capable of conducting an electric current through a solution, the one or more polymers including at least one PAMAM polymer configured to perform in-vivo electrochemical biomarker detection, wherein said at least one PAMAM polymer comprises:

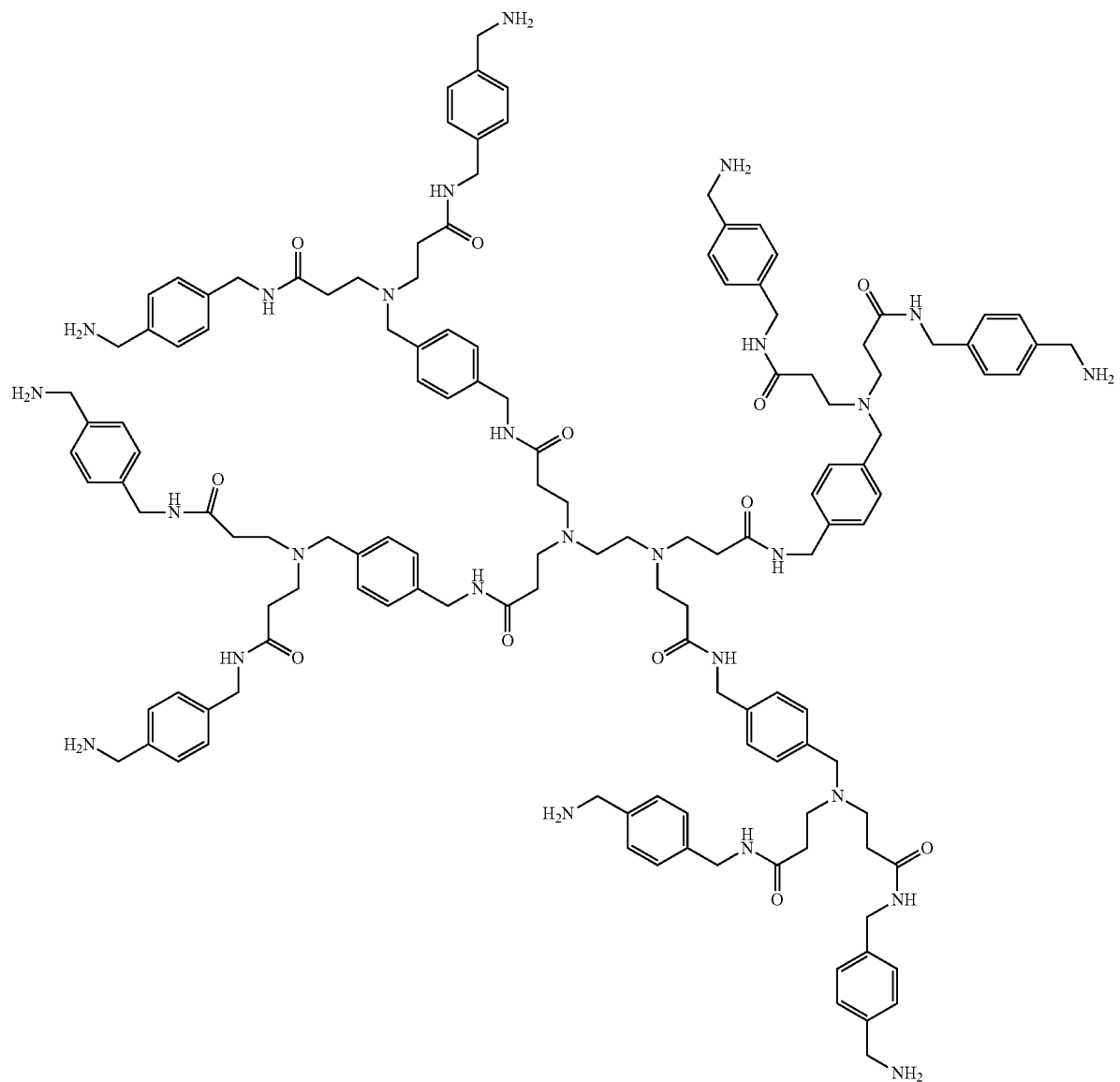 [SMILES: NCc1ccc(CNC(=O)CCN(CCC(=O)NCc2ccc(CN)cc2)Cc2ccc(CNC(=O)CCN(CCC(=O)NCc3ccc(CN(CCC(=O)NCc4ccc(CN)cc4)CCC(=O)NCc4ccc(CN)cc4)cc3)CCN(CCC(=O)NCc3ccc(CN(CCC(=O)NCc4ccc(CN)cc4)CCC(=O)NCc4ccc(CN)cc4)cc3)CCC(=O)NCc3ccc(CN(CCC(=O)NCc4ccc(CN)cc4)CCC(=O)NCc4ccc(CN)cc4)cc3)cc2)cc1]
* * * * *